US00PP16989P3

(12) United States Plant Patent

Clark et al.

(10) Patent No.: US PP16,989 P3

(45) Date of Patent: Aug. 15, 2006

(54) BLACKBERRY—APF-12 CULTIVAR

(50) Latin Name: ***Rubus* sp.**
Varietal Denomination: APF-12

(75) Inventors: John Reuben Clark, Fayetteville, AR (US); James Norman Moore, Fayetteville, AR (US)

(73) Assignee: University of Arkansas, Division of Agriculture, Fayetteville, AR (US)

( * ) Notice: Subject to any disclaimer, the term of this patent is extended or adjusted under 35 U.S.C. 154(b) by 77 days.

(21) Appl. No.: 10/815,437

(22) Filed: Mar. 30, 2004

(65) Prior Publication Data

US 2005/0223446 P1 Oct. 6, 2005

(51) Int. Cl.
*A01H 5/00* (2006.01)

(52) U.S. Cl. ..... Plt./203

(58) Field of Classification Search ..... Plt./203
See application file for complete search history.

*Primary Examiner*—Anne Marie Grunberg
*Assistant Examiner*—Georgia Helmer

(57) ABSTRACT

Description and specifications of a new and distinct blackberry variety which originated from seed produced by a a hand pollinated cross of Arapaho (U.S. Plant Pat. No. 8,510)×Arkansas selection 830 is provided. This new blackberry variety can be distinguished by its primocane-fruiting habit, potential high yields, medium to large fruit size, and good fruit quality.

3 Drawing Sheets

SUMMARY OF THE INVENTION

The new and distinct variety of blackberry originated from a hand pollinated cross of Arapaho (U.S. Plant Pat. No. 8,510)×Arkansas selection 830 made in 1994 at the Arkansas Agricultural Experiment Station Fruit Substation at Clarksville, Ark.

Plants and fruit of this new variety differ phenotypically from its parents. In comparison to both parents, the new variety is primocane fruiting (fruits on current-season canes) and second-year canes (floricane-fruiting) rather than only on second-year canes or floricane-fruiting as Arapaho and Arkansas selection 830. The canes of the new variety have thorns, a difference from the variety Arapaho. The new variety attained the primocane-fruiting trait allelles from both parents, even though neither parent expressed this recessive trait. The primocane-fruiting trait was originally attained from a wild selection named Hillquist (not patented) that was found at Ashland, Va., which was used later in breeding at the University of Arkansas in the late 1960s. Arapaho and Arkansas selection 830 both have Hillquist in their genetic backgrounds. The most outstanding trait of the new variety is its primocane-fruiting habit, a plant type not available on the commercial blackberry market at this time. The new variety also fruits on floricanes, as do all other existing blackberry varieties.

Although blackberries (*Rubus* sp.) are highly heterogeneous and outcrossing, and most clones contain genes from more than one species, the new variety and its progenitor lines phenotypically exhibit characters predominately of the erect eastern United States species, *Rubus allegheniensis* Porter (highbush blackberry) possibly introgressed with *R. argutus* Link. (tall blackberry).

The seeds resulting from this controlled hybridization were germinated in a greenhouse in the spring of 1995 and planted in a field on the Arkansas Agricultural Research and Extension Center, Fayetteville, Ark. The seedlings fruited during the summer of 1997 and one, designated APF-12, was selected for its primocane-fruiting habit, good fruit size, and good quality.

During the winter of 1997–98, the original plant selection was moved from the site of selection and propagated asexually from root cuttings, at the Arkansas Agricultural Experiment Station Fruit Substation at Clarksville, Ark., and two test rows of 20 plants each were established. Subsequently, additional test plantings have been established with asexually multiplied plants at three locations in Arkansas. Additionally, the variety has been tested at state experiment stations or U.S. Dept. of Agriculture—Agricultural Research Service sites in Aurora, Oreg., Geneva, N.Y., Griffin, Ga., West Lafayette, Ind., and Poplarville, Miss. and at each location propagation was from root cuttings. Data discussed are from testing at Clarksville, Ark. unless otherwise noted.

The new variety has been asexually multiplied annually since 1997 by the use of root cuttings. It forms new plants from adventitious buds on root cuttings more readily than its parent Arapaho. During all asexual multiplication, the characteristics of the original plant have been maintained and no aberrant phenotypes have appeared.

Test plantings over a wide geographic area have shown this new variety to be adapted to differing soil and climatic conditions. The primocane-fruiting trait has been expressed consistently in plants at all test sites.

Plants of the new variety are vigorous and prolific and row establishment following planting is rapid. Both primocanes and floricanes are erect in growth habit, and self-supporting, requiring no trellis support. Trellis support is beneficial at times of high fruit loads or windy conditions, when the canes may bend due to these circumstances. The plants are thorny. Plants and fruit are moderately tolerant to anthracnose [*Elsinoe veneta* (Burkh.) Jenkins], and plants appear immune to orange rust [*Gymnoconia nitens* (Schwein.) F. Kern and H. W. Thurston.]. Plants are susceptible to double blossom/rosette [*Cercosporella rubi* (Wint.) Plakidas]. The only fungicide applied to the test plants was liquid lime sulfur at budbreak, for the control of anthracnose. No insecticides were applied to the test plants.

The floricane bloom period of the new variety averages 0 to 1 day earlier than the variety APF-8 (U.S. Plant patent application Ser. No. 10/815,438), and earlier than the variety Arapaho. The average 10% first bloom date is April 22.

Floricane fruit of the new variety begins ripening 0 to 3 days earlier than the Arapaho, and 3 days earlier than the variety APF-8, and has a similar floricane fruiting period to these varieties of average 28 days, all based on testing at Clarksville, Ark. Average floricane first ripening date is June 7 in west-central Arkansas. Floricane fruit yields of the new variety are usually 5 to 7 lb/plant and are usually comparable to the variety APF-8 and significantly higher than the Arapaho variety (with yields of 3 to 4 lb/plant) at all test locations. Floricane yields are consistent from year to year, unless cold damage in winter or spring occurs that damages the floricanes or floricane buds.

Primocane first bloom date of the new variety averages June 17, near that of variety APF-8. Primocanes continue to bloom to varying degrees until frost at Clarksville, Ark. Primocane first bloom date in Aurora, Oreg., occurrs in late July, and continues consistently until frost in the fall.

Primocane fruit of the new variety ripens at different dates depending on location. At Clarksville, Ark., first ripe fruit on primocanes occurs on average July 17, near that of variety APF-8. Flowering and fruiting continues to a varying degree until the end of the growing season which is terminated usually in mid October (but can extend to late November) by frost at this location. At Aurora, Oreg., first primocane fruits ripen on average September 1, and are similar in ripening date to the variety APF-8. The plants continue to fruit and flower heavily until the termination of the growing season due to frost. Primocane fruit yields at Clarksville, Ark. average 1.0 lb/plant, approx. 0.5 lb plant less than variety APF-8 at this location. Primocane fruit yields at Aurora, Oreg. range from 2.3 to 9.5 lb/plant depending on plant age, near that of yields of the variety APF-8.

The fruit is conic/ovate to oblong in shape, glossy black in color and attractive. Some differences between primocane and floricane fruit have been observed, particularly based on location of where the plants are grown and temperature differences during the growing season for these locations. The floricane fruit is medium-large (4–5 g), similar to or 1.0 g smaller than the variety APF-8, and usually similar to the size of the Arapaho variety. Floricane fruit size of the new variety is maintained well throughout the entire harvest season. The new variety exhibits excellent floricane fruit fertility with full drupelet set. The floricane fruit is firm at maturity, rating more firm than the Shawnee (U.S. Plant Pat. No. 5,686) and Choctaw (U.S. Plant Pat. No. 6,678) varieties, but not as firm as the Arapaho variety.

Primocane fruit averages 4.2 g/berry for the new variety, 0.8 g smaller than variety APF-8 at Clarksville, Ark. Fruit quality is often lower than that of floricane fruits at this location, with the occurrence of poorer fruit color (more reddening and sunburn) and occasional double-fruited berries observed. Primocane fruit of the new variety in Aurora, Oreg. had an average size of 10 g, 1 g larger than that of variety APF-8. Fruit quality is consistent at this location, with uniform berry color and no double fruits as observed in Arkansas. The differences in fruit weight, yields, and quality among the two test locations is attributed to continuous very high daytime temperatures at Clarksville, Ark. (in excess of 90° F. for continuous days in August and early September) compared to Aurora, Oreg. where daytime maximum temperatures are lower. The high heat appears to impact fruit set and berry development, in addition to berry quality.

The fresh fruit rates good in flavor, being comparable to varieties APF-8 and Arapaho. The flavor is sweet and mildly subacid, with a distinct blackberry aroma. The soluble solids concentration of floricane fruit averages 7.9%, and primocane fruit 12.0%, with the floricane fruit soluble solids lower that the varieties APF-8 and Arapaho, while the primocane fruit soluble solids is higher than that for the variety APF-8. Floricane fruit dry seed weight averages 2.1 mg/seed, smaller than varieties APF-8 and Arapaho.

Floricane fruit clusters are medium-large, cymose, and are mostly borne on the periphery of the plant canopy, providing easy access to harvest. Flower fertility is high and clusters are well filled.

Primocane flowers and subsequent fruits usually first are borne on the cane terminus, and fruiting continues down the primocane during the season. Canes usually attain a cane length of 4.5 to 5 ft. prior to the appearance of flower buds. The number of nodes down the cane that develop flowers is largely dependent on the length of the growing season.

The new variety has been named the AFP-12 cultivar.

BRIEF DESCRIPTION OF THE PHOTOGRAPHS

The accompanying photographs show typical specimens of the floricane individual fruit (First Sheet of drawings Sheet 1), primocanes with flower buds (Second Sheet of drawings Sheet 2), and individual primocane leaf (Third Sheet of Drawings Sheet 3) of the new variety in color as nearly true as it is reasonably possible to make in a color illustration of this character.

DETAILED DESCRIPTION OF THE NEW VARIETY

The following is a detailed description of the botanical and pomological characteristics of the subject blackberry. Color data are presented in Royal Horticultural Society Colour Chart designations.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Medium.

*Growth habit.*—Canes erect; suckers from crown and roots.

*Growth rate.*—Primocanes reach tipping height (107 cm) in 53 days from emergence.

*Productivity.*—Floricane — 5–7 lb/plant and more productive than Arapaho (3–4 lb/plant). Primocane — 1.0 lb/plant, approx. 0.5 lb/plant less than APF-8; primocane yield at Aurora, Oreg. of 1.0 to 11.0 lb/plant, depending on year and age of plants; near that of APF-8 at this location.

*Cold hardiness.*—Hardy; floricane hardy to a mid-winder low of 10° F. (lowest temperature recorded during evaluation at Clarksville, Ark.).

*Canes.*—Thorny, erect. Floricane: Cane diameter: base 1.3 cm, midpoint 1.1 cm, terminal 0.9 cm. Internode length: base 5.1 cm, midpoint 4.4 cm, terminal 2.4 cm. Floricane (winter cane) color: base— Yellow Green Group (146B); midpoint— Yellow Green Group (146B); terminus — Yellow Green Group (146B). Thorn density (per 30 cm of cane length): base 43.2, midpoint 37.7, terminus 28.5. Primocane: Cane diameter: base 1.1 cm, midpoint 0.8 cm, terminal 0.3 cm. Internode length: base 3.4 cm, midpoint 3.6 cm, terminal 1.9 cm. Primocane color: base— Yellow Green Group (146B); midpoint— Yellow Green Group (146C); terminus— Yellow Green Group (146C). Thorn density (per 30 cm of cane length): base 51.5, midpoint 17.5, terminus 10.0. Date of primocane emergence: April 6 (Julian 97).

*Disease resistance.*—Moderate resistance to anthracnose; immune to orange rust; susceptible to double blossom/rosette.

Foliage:

*Primocane.*—

*Leaves.*—Mature compound leaf width 22.7 cm; length 20.0 cm.

*Leaflet.*—Width 7.9 cm; length 13.2 cm; shape ovate with acute apex and subcordate base; margin serrated, serration teeth length 0.3 cm, and width at base 0.4 cm; light pubescence on abaxial and very light on adaxial surface. Number of leaflets per compound leaf: 5. Color: Base abaxial— Yellow Green Group (147B); adaxial— Green Group (137A); midpoint abaxial— Yellow Green Group (146B); adaxial— Green Group (137A); terminal abaxial— Yellow Green Group (147B) adaxial— Green Group (137A).

*Petioles.*—Length: 5.8 cm. Color: Yellow Green Group (146C).

*Petiolules.*—Length: 3.8 cm. Color: Yellow Green Group (146C).

*Stipules.*—Length: 1.1 cm. Width: 0.09 cm.

*Floricane.*—

*Leaves.*—Mature compound leaf width 13.3 cm; length 13.7 cm.

*Leaflet.*—Width 5.3 cm; length 8.7 cm; shape ovate with acute apex and subcordate base; margin serrated, with serration teeth length 0.3 cm and width at base 0.2 cm; very light pubescence on abaxial and adaxial surfaces. Number of leaflets per compound leaf: 3. Color: base abaxial— Yellow Green Group (146B); adaxial— Green Group (137A); midpoint abaxial— Yellow Green Group (146A); adaxial— Yellow Green Group (147A); terminal abaxial— Yellow Green Group (146B); adaxial— Yellow Green Group (146A).

*Petioles.*—Length: 5.2 cm. Color: Yellow-Green Group (144A).

*Petiolules.*—Length 1.7 cm. Color: Yellow-Green Group (144A).

*Stipules.*—Length: 0.7 cm. Width: 0.1 cm.

Flowers:

*Floricanes.*—

*Date of bloom.*—10% April 22 (Julian 113); 50% — April 27 (Julian 118); Last — May 22 (Julian 143).

*Petal color.*—White Group (155C).

*Reproductive organs.*—Stamens — numerous. Pistils— numerous. Pollen— fertile abundant.

*Flower diameter.*—4.3 cm.

*Petal size.*—Length: 2.0 cm. Width: 1.7 cm.

*Average number flowers per cluster.*—7.1.

*Average number of petals per flower.*—5.

*Number of sepals per flower.*—5.

*Peduncle length.*—3.2 cm.

*Peduncle color.*—Yellow Green Group (146B).

*Cyme type.*—Corymbiform.

*Primocanes.*—

*Date of bloom.*—First — June 17 (Julian 169); Last — November 23 (Julian 328).

*Petal color.*—White Group (155C).

*Reproductive organs.*—Stamens — numerous. Pistils — numerous. Pollen — fertile and abundant.

*Flower diameter.*—3.7 cm.

*Petal size.*—Length: 1.8 cm. Width: 1.3 cm.

*Average number flowers per cluster.*—4.0.

*Average number of petals per flower.*—5.4.

*Number of sepals per flower.*—5.

*Peduncle length.*—2.2 cm.

*Peduncle color.*—Yellow-Green Group (144A).

*Cyme type.*—Corymbiform.

Fruit:

*Floricane.*—

*Maturity.*—Average first ripe date is June 7. Average period of ripening is June 7 to July 5.

*Size.*—Average 4.9 g. Diameter: Fruit at primary position on inflorescence: equator 1.8 cm, base pole 1.8 cm, terminal pole 1.6 cm; fruit at secondary positions on inflorescence: equator 1.7 cm., base pole 1.6 cm, terminal pole 1.3 cm. Length (Primary fruit) 2.3 cm.

*Shape.*—Conic/ovate to oblong.

*Color.*—Glossy black; Black Group (202A).

*Drupelet size.*—Medium, 0.5 cm.

*Seed weight.*—2.5 mg (dry wt., individual seed).

*Soluble solids.*—7.9%.

*pH.*—3.2 (as measured by pH meter on undiluted juice from a sample of 25 fully-ripe berries).

*Acidity.*—0.81 g tartaric acid/100 ml.

*Processed quality.*—Not evaluated in processing.

*Uses.*—Fresh is main use but can be processed for jellies, jams, juice, wine.

*Primocane.*—

*Maturity.*—Average first ripe date is July 17. Average period of ripening is July 17 until frost at approximately October 15 to late November depending on year at Clarksville, Ark.

*Size.*—Average 4.2 g. Diameter: Fruit at primary position on inflorescence: equator 2.3 cm, base pole 2.0 cm, terminal pole 2.0 cm; fruit at secondary positions on inflorescence: equator 2.0 cm., base pole 2.0 cm, terminal pole 1.8 cm. Length (Primary fruit) 1.8 cm.

*Shape.*—Conic-ovate.

*Color.*—Glossy black; Black Group (202A).

*Drupelet size.*—Medium, 0.6 cm.

*Seed weight.*—2.6 mg (dry wt., individual seed).

*Soluble solids.*—12.0%.

*pH.*—3.2 (as measured by pH meter on undiluted juice from a sample of 25 fully-ripe berries).

*Acidity.*—0.71 g tartaric acid/100 ml.

*Processed quality.*—Not evaluated in processing.

*Uses.*—Fresh is main use but can be processed for jellies, jams, juice, wine.

The variety: The most distinctive features of the variety are its primocane-fruiting habit, potential high yields, medium to large fruit size, and good fruit quality.

We claim:

1. A new and distinct variety of blackberry plant, substantially as illustrated and described, characterized by its primocane-fruiting habit, potential high yields, medium to large fruit size, and good fruit quality.

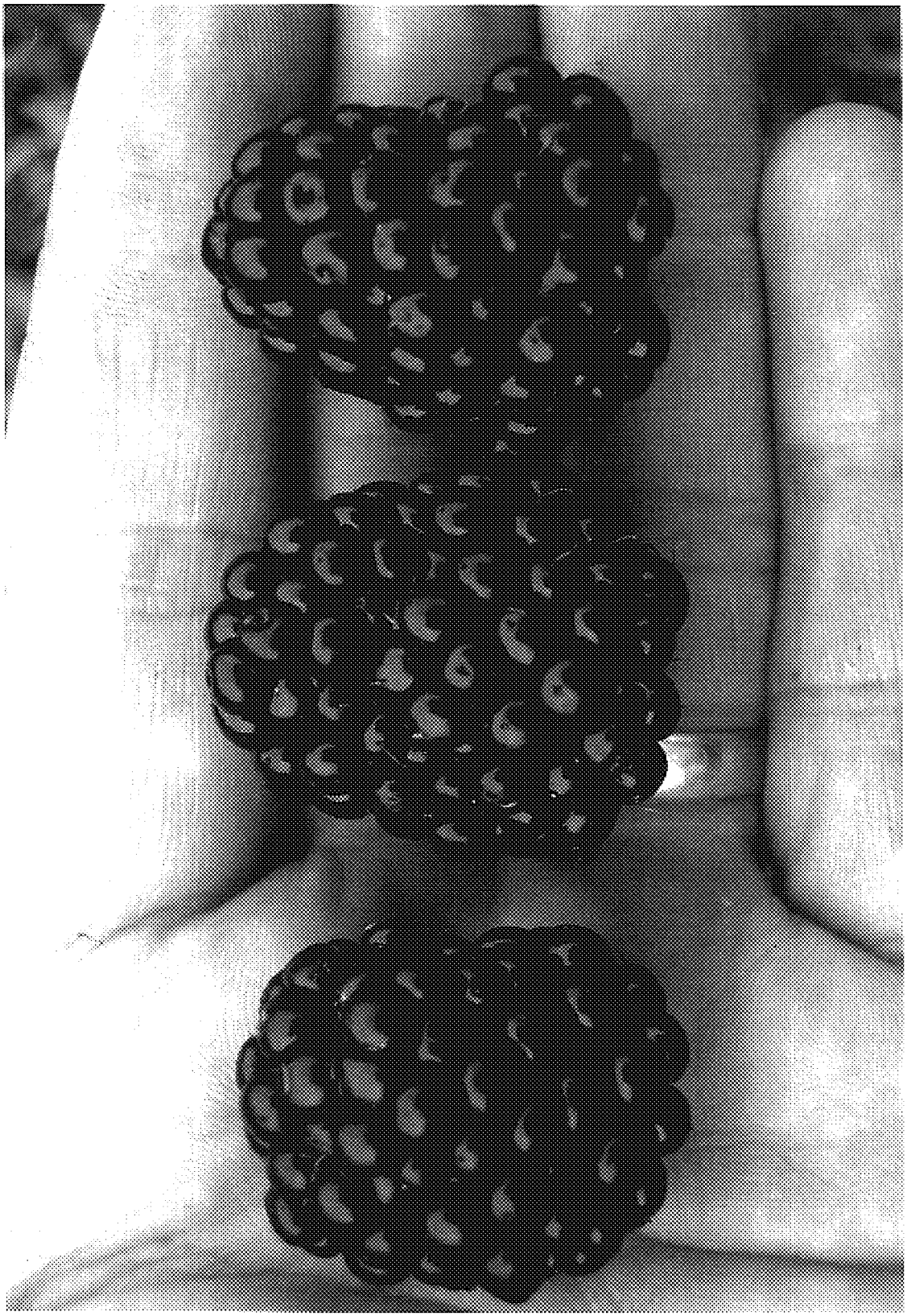

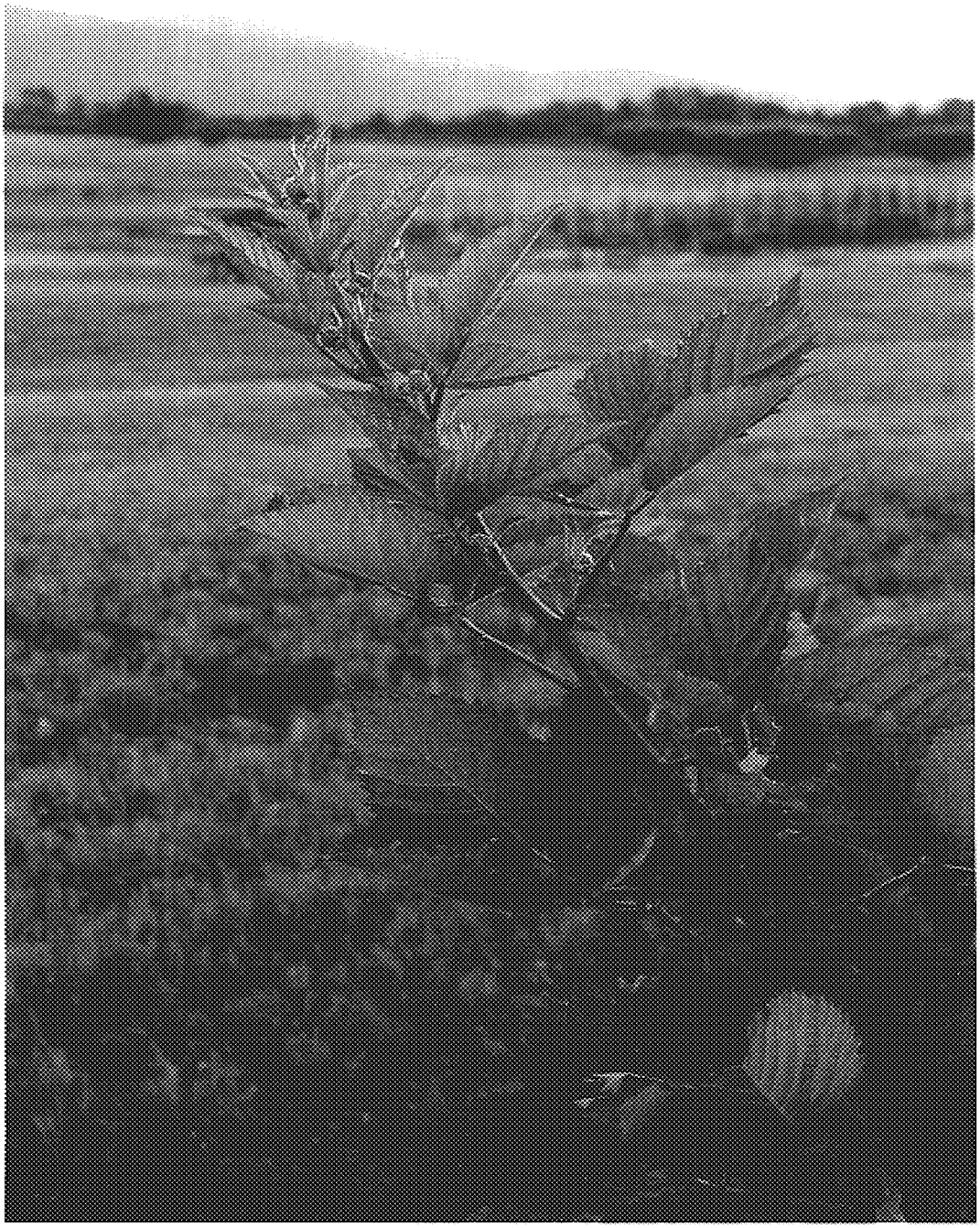

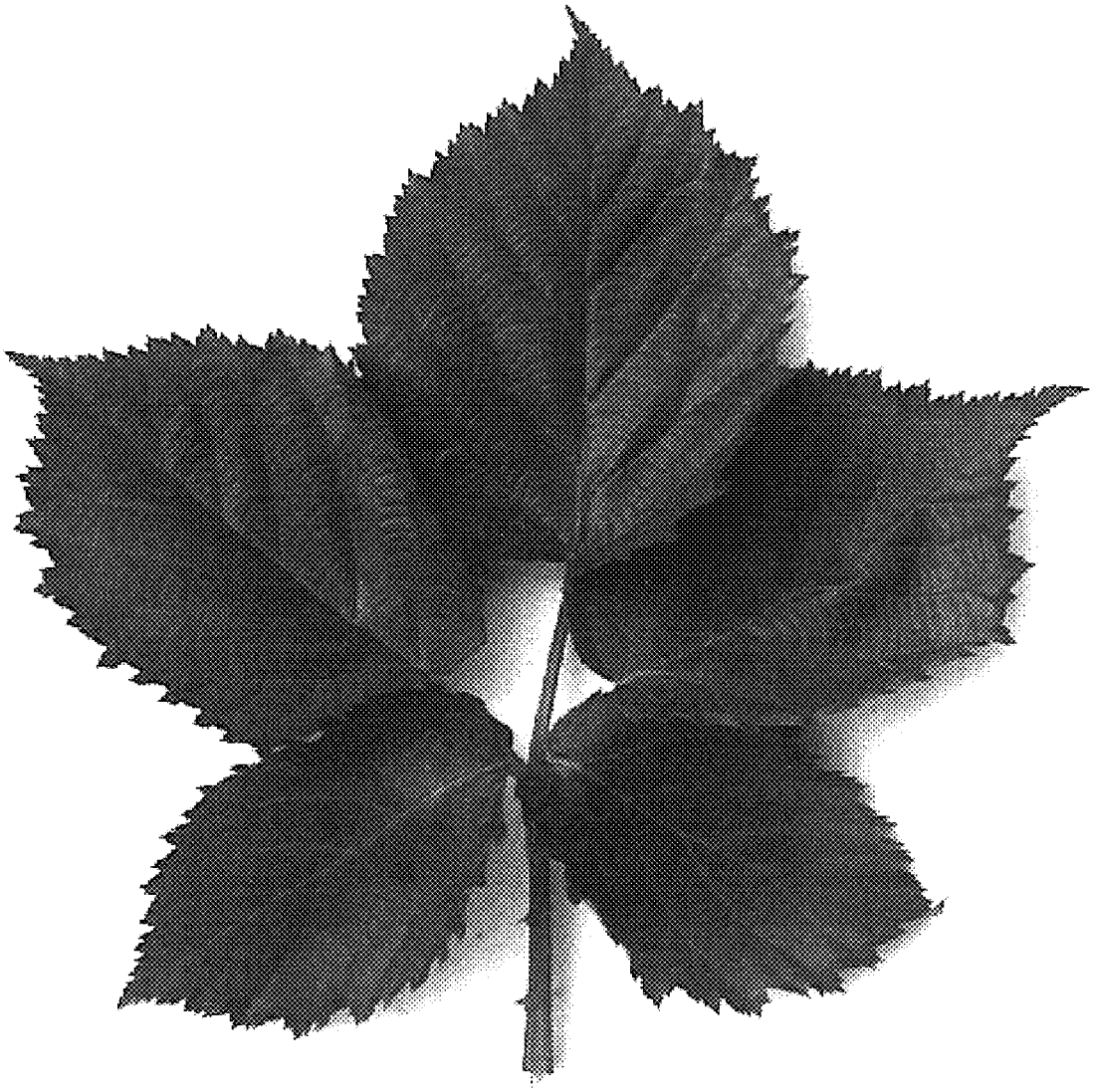

* * * * *